United States Patent
AlQuraishi

(10) Patent No.: US 11,581,060 B2
(45) Date of Patent: Feb. 14, 2023

(54) PROTEIN STRUCTURES FROM AMINO-ACID SEQUENCES USING NEURAL NETWORKS

(71) Applicant: President and Fellows of Harvard College, Cambridge, MA (US)

(72) Inventor: Mohammed AlQuraishi, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 504 days.

(21) Appl. No.: 16/735,354

(22) Filed: Jan. 6, 2020

(65) Prior Publication Data

US 2020/0234788 A1 Jul. 23, 2020

Related U.S. Application Data

(60) Provisional application No. 62/788,435, filed on Jan. 4, 2019.

(51) Int. Cl.
*G16B 15/00* (2019.01)
*G16B 45/00* (2019.01)

(52) U.S. Cl.
CPC .......... *G16B 15/00* (2019.02); *G16B 45/00* (2019.02)

(58) Field of Classification Search
USPC .......................................... 702/19
See application file for complete search history.

(56) References Cited

U.S. PATENT DOCUMENTS

| 8,207,316 B1* | 6/2012 | Bentwich | C12N 15/1131 435/375 |
|---|---|---|---|
| 2003/0198997 A1* | 10/2003 | Von Dreele | G01N 23/207 435/7.1 |
| 2004/0204861 A1* | 10/2004 | Benner | G16B 10/00 702/19 |
| 2007/0077553 A1* | 4/2007 | Bentwich | C12Q 1/703 435/5 |
| 2008/0183452 A1* | 7/2008 | Parida | G16B 15/20 703/11 |
| 2021/0319851 A1* | 10/2021 | Mukhopadhyay | G16B 40/00 |
| 2022/0165360 A1* | 5/2022 | Lee | G16H 70/20 |

OTHER PUBLICATIONS

Ramachandran G.N., et al., "Stereochemistry of polypeptide chain configurations," Mol. Biol. 1963; 7: 95-99.
Bernstein F.C., et al., "The Protein Data Bank. A computer-based archival file for macromolecular structures," Eur. J. Biochem. 1977; 80: 319-324.

(Continued)

*Primary Examiner* — Pierre E Elisca
(74) *Attorney, Agent, or Firm* — Nixon Peabody LLP; David S. Resnick; Wayne L. Tang

(57) ABSTRACT

The present disclosure provides for systems and methods for generating and displaying a three dimensional map of a protein sequence. An exemplary method can provide for using deep learning models to predict protein folding and model protein folding using three dimensional representations. The method more effectively exploits the potential of deep learning approaches. The method approach overall involves three stages—computation, geometry, and assessment.

12 Claims, 2 Drawing Sheets

(56) References Cited

OTHER PUBLICATIONS

Dill K.A., "Dominant forces in protein folding," Biochemistry. 1990; 29: 7133-7155.
Moult J., et al., "A large-scale experiment to assess protein structure prediction methods," Proteins. 1995; 23 (ii-iv).
Hochreifer S., Schmidhuber J., "Long short-term memory," Neural Comput. 1997; 9: 1735-1780.
Ponting C.P., Russell R.R., "The natural history of protein domains," Annu. Rev. Biophys. Biomol. Struct. 2002; 31: 45-71.
Zhang Y., Skolnick J., "Scoring function for automated assessment of protein structure template quality," Proteins. 2004; 57: 702-710.
Contreras-Mereira B., et al., "Empirical limits for template-based protein structure prediction: the CASPS example," FEBS Lett. 2005; 579: 1203-1207.
Parsons J., et al., "Practical conversion from torsion space to Cartesian space for in silico protein synthesis," J. Comput. Chem. 2005; 26: 1063-1068.
Xu J., Zhang Y., "How significant is a protein structure similarity with TM-score=0.5?," Bioinformatics. 2010; 26: 889-895.
Zhao F., et al., Fragment-free approach to protein folding using conditional neural fields, Bioinformatics. 2010; 26: i310-i317.
Gajda M.J., et al., "Protein structure prediction: from recognition of matches with known structures to recombination of fragments," in: Kolinski A. Multiscale Approaches to Protein Modeling. Springer, 2011: 231-254.
Gejda M.J., et al., "Multiscale Approaches to Protein Modeling," Springer, 2011.
Leaver-Fay A., et al., "ROSETTA3: an object-oriented software suite for the simulation and design of macromolecules," Meth. Enzymol. 2011; 487: 545-574.
Marks D.S., et al., "Protein 3D structure computed from evolutionary sequence variation," PLoS One. 2011; 6: e28766.
Zhou Y., et al., "Trends in template/fragment-free protein structure prediction," Theor. Chem. Acc. 2011; 128: 3-16.
Aydin Z., et al., (2012). "Protein torsion angle class prediction by a hybrid architecture of Bayesian and neural networks," 13th International Conference on Bioinformatics and Computational Biology, pp. 2012-2018.
Dill K.A., MacCallum J.L., "The protein-folding problem, 50 years on." Science. 2012; 338: 1042-1046.
Marx D., Hutter J., "Ab Initio Molecular Dynamics: Basic Theory and Advanced Methods," Cambridge University Press, 2012.
Xu D., Zhang Y., "Ab initio protein structure assembly using continuous structure fragments and optimized knowledge-based force field," Proteins. 2012; 80: 1715-1735.
Juan D., et al., "Emerging methods in protein co-evolution," Nat. Rev. Genet. 2013; 14: 249-261.
Simonyan K., et al., "Deep inside convolutional networks: visualising image classification models and saliency maps," Arxiv. 2013; (arXiv:1312.6034V2), https://arxiv.org/abs/1312.6034.
Hopf T.A., et al., "Sequence co-evolution gives 3D contacts and structures of protein complexes," Elife. 2014; 3.
Lyons J., et al., "Predicting backbone Cα angles and dihedrals from protein sequences by stacked sparse auto-encoder deep neural network," J. Comput. Chem. 2014; 35: 2040-2046.
Adhikari B., et al., "CONFOLD: residue-residue contact-guided ab initio protein folding," Proteins. 2015; 83: 1436-1449.
Alva V., et al., "A vocabulary of ancient peptides at the origin of folded proteins," Elife. 2015; 4: e09410.
LeCun Y., et al., "Deep learning," Nature. 2015; 521: 436-444.
Yang J., et al., "The I-TASSER suite: protein structure and function prediction," Nat. Methods. 2015; 12: 7-8.
Abadi M., et al., (2016). "TensorFlow: a system for large-scale machine learning," 12th USENIX Symposium on Operating Systems Design and Implementation (OSDI 16), pp. 265-283.
Alain G., Bengio Y., "Understanding intermediate layers using linear classifier probes," Arxiv. 2016; (arXiv:1610.01644v4), https://arxiv.org/abs/1610.01644.
Kryshtafovych A., et al, "CASP11 statistics and the prediction center evaluation system," Proteins. 2016; 84: 15-19.
Nguyen A., et al., "Multifaceted feature visualization: uncovering the different types of features learned by each neuron in deep neural networks," Arxiv. 2016; (arXiv:1602.03616v2). https://arxiv.org/abs/1602.03616.
Ovchinnikov S., et al., "Improved de novo structure prediction in CASP11 by incorporating coevolution information into Rosetta," Proteins. 2016; 84: 67-75.
Perez A., et al., "Blind protein structure prediction using accelerated free-energy simulations," Sci. Adv. 2016; 2: e1601274.
Dawson N.L., et al., "CATH: an expanded resource to predict protein function through structure and sequence," Nucleic Acids Res. 2017; 45: D289-D295.
Gao Y., et al., "Real-value and confidence prediction of protein backbone dihedral angles through a hybrid method of clustering and deep learning," Arxiv. 2017; (arXiv:1712.07244v1), https://arxiv.org/abs/1712.07244v1.
Hopf T.A., et al., "Mutation effects predicted from sequence covariation," Nat. Biotech. 2017; 35: 128-135.
Koh P.W., Liang P., "Understanding Black-box predictions via influence functions," Arxiv. 2017; (arXiv:1703.04730v2), https://arxiv.org/abs/1703.04730.
Li H., et al., "Deep learning methods for protein torsion angle prediction," BMC Bioinformatics. 2017; 18: 417.
Ovchinnikov S., et al., "Protein structure determination using metagenome sequence data," Science. 2017; 355: 294-298.
Shrikumar A., et al., (2017). "Learning important features through propagating activation differences," ICML'17 Proceedings of the 34th International Conference on Machine Learning-Volume 70, pp. 3145-3153.
Wang S., et al., "Accurate de novo prediction of protein contact map by ultra-deep learning model," PLoS Comput. Biol. 2017; 13: e1005324.
Kryshtafovych A., et al., "Evaluation of the/template-based modeling in CASP12," Proteins. 2018; 86: 321-334.
Liu T., et al., "Biological and functional relevance of CASP predictions," Proteins. 2018; 86: 374-386.
Liu Y., et al., "Enhancing evolutionary couplings with deep convolutional neural networks," Cell Syst. 2018; 6: 65-74.
Moult J., et al., "Critical assessment of methods of protein structure prediction (CASP)-round XII," Proteins. 2018; 86: 7-15.
Schaarschmidt J., et al., "Assessment of contact predictions in CASP12: co-evolution and deep learning coming of age," Proteins. 2018; 86: 51-66.
Zhang C., et al., "Template-based and free modeling of I-TASSER and Quark pipelines using predicted contact maps in CASP12," Proteins. 2018; 86: 136-151.
AlQuraishi M., "Parallelized natural extension reference frame: parallelized conversion from internal to Cartesian coordinates," J. Comp. Chem. 2019; 40: 885-892.
AlQuraishi M., "ProteinNet: a standardized data set for machine learning of protein structure," ArXiV. 2019; (arXiv:1902.00249v1), https://arxiv.org/abs/1902.00249.

* cited by examiner

PROTEIN STRUCTURES FROM AMINO-ACID SEQUENCES USING NEURAL NETWORKS

PRIORITY CLAIM

This application claims priority from U.S. Provisional Application 62/788,435, filed Jan. 4, 2019. The entirety of that application is hereby incorporated by reference.

GOVERNMENT FUNDING

This invention was made with government support under GM 107618 awarded by the National Institutes of Health. The government has certain rights in the invention.

FIELD

The present invention is directed to protein sequencing. In particular, using deep learning models to predict protein folding and model protein folding using three dimensional representations.

BACKGROUND

The following description includes information that may be useful in understanding the present invention. It is not an admission that any of the information provided herein is prior art or relevant to the presently claimed invention, or that any publication specifically or implicitly referenced is prior art.

Proteins are linear polymers that fold into very specific and ordered three dimensional conformations based on their amino acid sequences. Understanding how this occurs is a foundational problem in biochemistry. Computational approaches to protein folding not only seek to make structure determination faster and less costly; they aim to understand the folding process itself. Existing computational methods fall into two broad categories. The first category builds explicit sequence-to-structure maps using computational procedures to transform raw amino acid sequences into 3D structures. This includes physics-based molecular dynamics simulations, which are restricted by computational cost to small proteins, and fragment-assembly methods, which find energy-minimizing conformations by sampling statistically derived protein fragments. Fragment assembly usually achieves high accuracy only when homologous protein structures are used as templates. Such template-based methods use one or more experimental structures—found through homology searches—as the basis for making predictions.

The second category of methods eschews explicit sequence-to-structure maps and instead identifies co-evolving residues within protein families to derive residue-residue contact maps, using co-evolution as an indicator of contact in physical space. With a large and diverse set of homologous sequences—typically tens to hundreds of thousands of amino acids—co-evolution methods can accurately predict contact maps. It has been found that a correct contact map can guide fragment assembly methods to an accurate 3D structure 25-50% of the time. However, because co-evolutionary methods do no construct a model of the relationship between individual sequences and structures, they are unable to predict structures for which no sequence homologs exist, as in new bacterial taxa or de novo protein design. Moreover, even for well-characterized proteins, such methods are generally unable to predict the structural consequences of minor sequence changes such as mutations or insertions/deletions ("indels"), because they operate on protein families rather than individual sequences (although they show promise in predicting the functional consequences of mutations).

End-to-end differentiable deep learning has revolutionized computer vision and speech recognition, but protein structure pipelines utilizing this approach continue to resemble the ways in which computers tackled vision and speech prior to deep learning, by having many human-engineered stages, each independently optimized. End-to-end differentiable models replace all components of such pipelines with differentiable primitives to enable joint optimization from input to output. In contrast, use of deep learning for structure prediction has so far been restricted to individual components within a larger pipeline, e.g., prediction of contact maps. This stems from the technical challenge of developing an end-to-end differentiable model that rebuilds the entire structure prediction pipeline using differentiable primitives. Accordingly, there remains a substantial need for new and potentially better approaches to prediction of protein folding, and in particular to more effective exploitation of the potential of deep learning approaches.

SUMMARY

The present disclosure provides a system for displaying a three dimensional map of a protein sequence. The system can include a display, a memory that contains machine readable medium and machine executable code having stored thereon instructions, and a control system coupled to the memory having one or more processors.

In some examples, the control system executes the machine executable code to cause the one or more processors to first receive molecular data comprising a set of amino acid residues of a protein. In some examples, the control system then processes the set of amino acid residues using a recurrent geometric network. The control system may then output a three dimensional map of the protein comprising three dimensional Cartesian coordinates. The control system may also display the three dimensional map on the display.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

Figure 1:
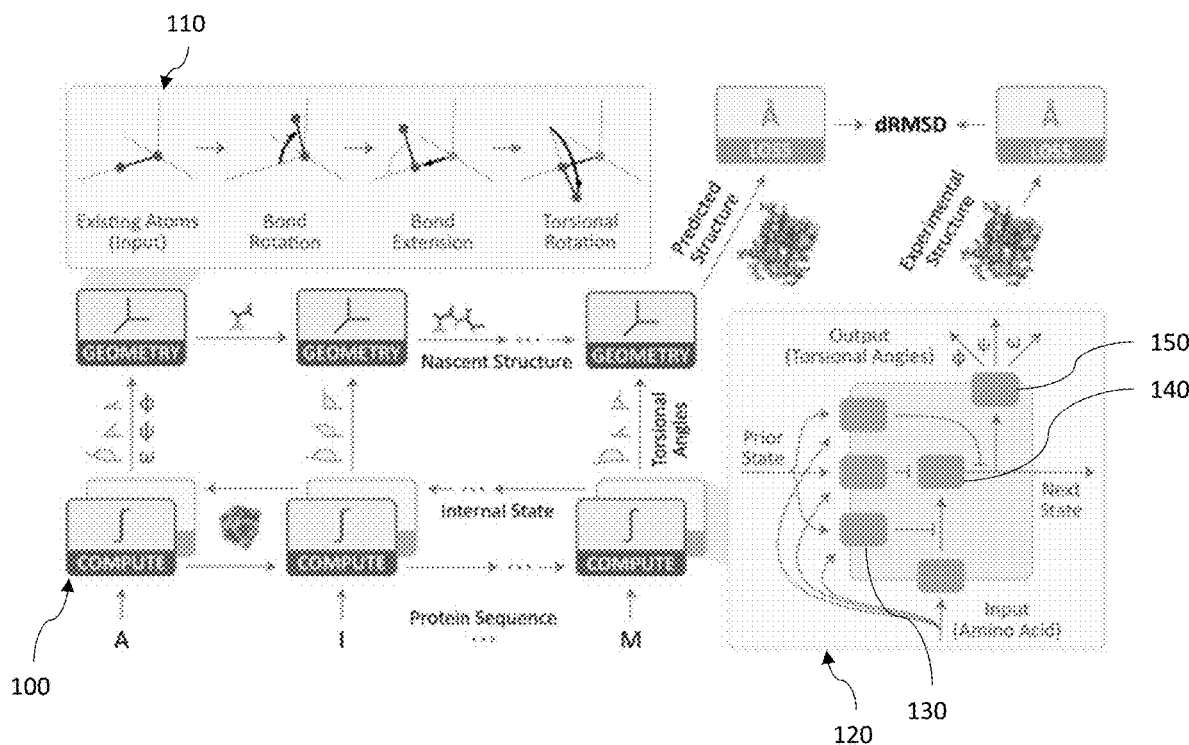
FIG. 1 depicts, in accordance with various embodiments of the present invention, a diagram of a process designed to output a 3D structure of a protein.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

INCORPORATION BY REFERENCE

Examples of protein structure learning are described in, for example, AlQuraishi, End-to-End Differentiable Learning of Protein Structure, Cell Systems, 10.1016/j.cels.2019.03.006, (2019), which is incorporated by reference herein in its entirety Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Overview

The present approach provides an end-to-end differentiable model of protein structure. The model couples local and global protein structure via geometric units that optimize global geometry without violating local covalent chemistry, and reflects four building blocks: (i) encoding protein sequence using a recurrent neural network, (ii) parameterizing (local) protein structure by torsional angles to enable a model to reason over diverse conformations without violating their covalent chemistry, (iii) coupling local protein structure to its global representation via recurrent geometric units, and (iv) using a differentiable loss function to capture deviations between predicted and experimental structures. This approach may outperform other methods in predicting novel folds even based on primary sequences and position-specific scoring matrices (PSSMs) that summarize individual residue propensities for mutation.

Conventional structure-prediction pipelines are multi-staged, first detecting domains that can be separately modelled, and running multiple algorithms to estimate secondary structure propensities, solvent accessibility, and disordered regions. Co-evolutionary methods use multiple sequence alignments to predict contact maps, and template-based methods search the Protein Data Bank (PDB) for templates. Their predictions are converted into geometric constraints to guide a conformation sampling process, where fragments are swapped in and out of putative structures to minimize an expertly-derived energy model. Due to this complexity, prediction times range from several hours to days, and require codebases as large as several million lines of code (Leaver-Fay et al., 2011).

In contrast, various techniques in accordance herewith utilize a single mathematical function that is evaluated once per prediction. Computation of this function implicitly carries out domain splitting, property finding, energy minimization, and conformational sampling simultaneously. Once trained, the computational structures described below make predictions 6-7 orders of magnitude faster than existing pipelines. This speed enables multiple new types of applications. For example, in protein design, where a protein sequence is selected to fold into a pre-specified three-dimensional fold, a very large number of test sequences must ordinarily be evaluated until a suitable candidate is found. Current approaches, consuming on the order of hundreds to tens of thousands of compute hours per single protein, make it impractical to rapidly explore large design spaces. Recurrent geometric network's (RGN) speed therefore greatly enhances the computational efficiency of analyzing protein design space, facilitating substantially greater exploration thereof. In virtual screening for small molecules, putative drugs are docked into in silico protein structures to find molecules that modulate protein function in a desired fashion. Due to the current computational cost of predicting protein structures, they are typically held in a fixed conformation, and only the small molecule is allowed to be conformationally flexible. This limits the applicability of such approaches, as proteins are flexible under physiological conditions. RGNs can make it computationally feasible to sample conformationally flexible proteins and small molecules. In variant prediction, where the structural consequences of an amino acid mutation in a protein is sought, existing co-evolutionary approaches are limited as they operate at the level of protein families, and thus have limited utility in predicting sequence-specific changes. RGNs, by contrast, do not utilize co-evolutionary information, and are better suited to making sequence-specific predictions.

Recurrent Geometric Networks

In various embodiments, systems and methods in accordance herewith take as input a sequence of amino acids and PSSMs and output a 3D structure. The overall approach involves three stages—computation, geometry, and assessment—that are herein referred to as a recurrent geometric network (RGN). The first stage utilizes computational units that, for each residue position, integrate information about its amino acid and PSSM with information coming from adjacent units. By laying these units in a recurrent bidirectional topology as shown in the below figure, the computations for each residue integrate information from residues upstream and downstream all the way to the N- and C-terminus of the protein, covering its entirety.

FIG. 1 illustrates an embodiment of the process a system may utilize to automatically classify image frames or sets of frames into behavioral modules. Protein sequences are fed one residue at a time to the computational units of an RGN 100, which compute an internal state that is integrated with the states of adjacent units. Based on these computations, torsional angles are predicted and fed to geometric units, which sequentially translate them into Cartesian coordinates to generate the predicted structure. dRMSD is used to measure deviation from experimental structures, serving as the signal for optimizing RGN parameters. The geometric units 110 take new torsional angles and a partial backbone chain, and extend it by one residue. The computational units 120, based on Long Short-Term Memory (LSTMs), use gating units 130 to control information flow in and out of the internal state 140, and angularization units 150 to convert raw outputs into angles.

Figure 2:
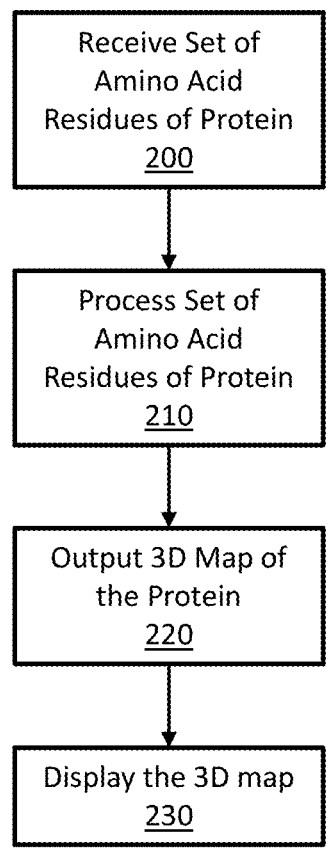
FIG. 2 depicts, in accordance with various embodiments of the present invention, a flow chart showing processing steps performed on amino acid residues.

FIG. 2 illustrates an embodiment of a process the system may perform to generate a three dimensional map of a protein after receiving a set of amino acid residues of protein 200. In some examples, the system may first receive a set of amino acid residues that may include a data file. In some examples, after being received, the set of amino acid residues of protein may be processed 210 using a recurrent geometric network and one or more processors. The system may then determine an internal state for each residue of the set of amino acid residues and integrate the internal state with the states of adjacent amino acid residues for each residue of the set of amino acid residues. The processed set of amino acid residues 210 may then be output as a data file including three dimensional map of the protein 220 generated by the system processing predicted torsional angles of the amino acid residue. The predicted torsional angles may be fed to geometric units. The geometric units may be sequentially translated into three dimensional Cartesian coordinates. The three dimensional map of the protein may then be displayed 230. The three dimensional map may also be stored in a memory.

Further stacking units in multiple layers implicitly encodes a multi-scale representation of proteins. Each unit outputs three numbers, corresponding to the torsional angles of the residue. It is not necessary to specify a priori how angles are computed. Instead, each unit's computation is described by an equation whose parameters are optimized so that RGNs accurately predict structures.

The second stage includes geometric units that take as input the torsional angles for a given residue and the partially completed backbone resulting from the geometric unit upstream of it, and output a new backbone extended by one residue, which is fed into the adjacent downstream unit. The last unit outputs the completed 3D structure of the protein. During model training, a third stage computes deviations between predicted and experimental structures using the distance-based root mean square deviation (dRMSD) metric. The dRMSD first computes pairwise distances between all atoms in the predicted structure and all atoms in the experimental one (separately), and then computes the root mean square of the distance between these sets of distances. Because dRMSD is distance-based, it is invariant to reflections, which can lead RGNs to predict reflected structures (effectively wrong chirality) that are corrected by a counter-reflection. RGN parameters may be optimized to minimize the dRMSD between predicted and experimental structures using backpropagation. Hyperparameters, which describe higher-level aspects of the model such as the number of computational units, may be determined through manual exploration of hyperparameter space.

A key limitation of explicit sequence-to-structure maps, including molecular dynamics and fragment assembly, is a reliance on fixed energy models that do not learn from data; a second limitation is the exclusive use of single-scale atomic or residue-level representations. In contrast, modern co-evolution methods leverage learning and multi-scale representations to substantially improve performance. RGNs go one step further by building a fully differentiable map extending from sequence to structure with all of the steps in existing prediction pipelines implicitly encoded and learnable from data. Through their recurrent architecture, RGNs can capture sequence-structure motifs and multiple scales from residues to domains. When tracking structure prediction during RGN training, RGNs appear to first learn global aspects of protein folds, then refine their predictions to generate more accurate local structure.

RGNs are multi-representational, operating on three distinct parameterizations of protein structure. The first is torsional, capturing local relationships between atoms with bond lengths and angles held fixed, and torsional angles as the immediate outputs of computational units. This virtually guarantees that predictions are structurally correct at a local level. The second is Cartesian, built by geometric units and capturing the global coordination of multiple atoms in 3D space, the catalytic triad of an enzyme's active site for example, even if the residues are distant along the protein chain. Future augmentations—e.g. 3D convolutional networks that operate directly on the Cartesian representation—may further improve the detection and quality of long-range interactions. The third parameterization, built in the dRMSD stage, is the matrix of inter-atomic distances, and is simultaneously local and global. It is useful for optimizing RGN parameters de novo, as we have used it, but can also be used to incorporate prior knowledge expressible in terms of atomic distances; such knowledge includes physical features (e.g. electrostatics) and statistical data on interactions (e.g. evolutionary couplings).

One limitation of current RGNs is their reliance on PSSMs, which have been found to be helpful to achieving high accuracy predictions. PSSMs are weaker than multiple sequence alignments as they are based on single residue mutation frequencies and ignore how each residue mutates in response to all other residues. Co-evolutionary couplings require pairwise frequencies, resulting in quadratically rather than linearly scaling statistical cost. Nonetheless, removing PSSMs and relying exclusively on raw sequences could robustify RGNs for many applications, including prediction of genetic variants. For protein design, RGNs can be used directly, by fixing the desired structure and optimizing the raw sequence and PSSMs to match it (i.e. by computing derivatives of the inputs—as opposed to model parameters—with respect to the dRMSD between predicted and desired structures.) Co-evolution methods do not have this capability as their inputs are the inter-residue couplings themselves, making the approach circular.

The history of protein structure prediction suggests that new methods complementary to existing ones are eventually incorporated into hybrids. RGNs have this benefit, being an almost entirely complementary modeling approach. For example, structural templates or co-evolutionary information could be incorporated as priors in the distance-based parameterization or even as raw inputs for learning. RGNs can also include secondary structure predicted by other algorithms. This is likely to be advantageous since the RGNs described here often predict global fold correctly but do less well with secondary structure. RGNs can also be made to predict side-chain conformations, by outputting a branched curve in lieu of the current linear curve, and are applicable to a wide range of other polymers (e.g. RNA tertiary structure.)

RGN Design

A protein of length L may be featurized as a sequence of vectors $(x_1, \ldots, x_L)$ where $x_t \in \mathbb{R}^d$ for all t. The dimensionality d is 41, where 20 dimensions are used as a one-hot indicator of the amino acid residue at a given position, another 20 dimensions are used for the PSSM of that position, and 1 dimension is used to encode the information content of the position. The PSSM values are sigmoid-transformed to lie between 0 and 1. The sequence of input vectors is fed to an LSTM whose basic formulation is described by the following set of equations.

$$i_t = \sigma(W_i[x_t, h_{t-1}] + b_i)$$

$$f_t = \sigma(W_f[x_t, h_{t-1}] + b_f)$$

$$o_t = \sigma(W_o[x_t, h_{t-1}] + b_o)$$

$$\tilde{c}_t = \tanh(W_c[x_t, h_{t-1}] + b_c)$$

$$c_t = i_t \odot \tilde{c}_t + f_t \odot c_{t-1}$$

$$h_t = o_t \odot \tanh(c_t)$$

$W_i$, $W_f$, $W_o$, $W_c$ are weight matrices, $b_i$, $b_f$, $b_o$, $b_c$ are bias vectors, $h_t$ and $c_t$ are the hidden and memory cell state for residue t, respectively, and $\odot$ is element-wise multiplication. Some embodiments use two LSTMs, running independently in opposite directions (1 to L and L to 1), to output two hidden states $h_t^{(f)}$ and $h_t^{(b)}$ for each residue position t corresponding to the forward and backward directions. Depending on the RGN architecture, these two hidden states are either the final outputs states or they are fed as inputs into one or more LSTM layers.

The outputs from the last LSTM layer form a sequence of a concatenated hidden state vectors $([h_t^{(f)}, h_t^{(b)}], \ldots, [h_L^{(f)}, h_L^{(b)}])$. Each concatenated vector is then fed into an angularization layer described by the following set of equations:

$$p_t = \text{softmax}(W_\varphi[h_t^{(f)}, h_t^{(b)}] + b_\varphi)$$

$$\varphi_t = \arg(p_t \exp(i\Phi))$$

$W_\varphi$ is a weight matrix, $b_\varphi$ is a bias vector, $\Phi$ is a learned alphabet matrix, and arg is the complex-valued argument function. Exponentiation of the complex-valued matrix $i\Phi$ is performed element-wise. The $\Phi$ matrix defines an alphabet of size m whose letters correspond to triplets of torsional angles defined over the 3-torus. The angularization layer interprets the LSTM hidden state outputs as weights over the alphabet, using them to compute a weighted average of the letters of the alphabet (independently for each torsional angle) to generate the final set of torsional angles $\varphi_t \in S^1 \times S^1 \times S^1$ for residue t (we are overloading the standard notation for protein backbone torsional angles, with $\varphi_t$ corresponding to the ($\psi$, $\varphi$, $\omega$) triplet). Note that $\varphi_t$ may be alternatively computed using the following equation, where the trigonometric operations are performed element-wise:

$$\varphi_t = \text{atan2}(p_t \sin(\Phi), p_t \cos(\Phi))$$

In general, the geometry of a protein backbone can be represented by three torsional angles $\varphi$, $\psi$, and $\omega$ that define the angles between successive planes spanned by the N, $C^\alpha$, and C' protein backbone atoms. While bond lengths and angles vary as well, their variation is sufficiently limited that they can be assumed fixed. Similar claims hold for side chains as well. The resulting sequence of torsional angles $(\varphi_1 \ldots \varphi_L)$ from the angularization layer is fed sequentially, along with the coordinates of the last three atoms of the nascent protein chain $(c_1 \ldots c_{3t})$, into recurrent geometric units that convert this sequence into 3D Cartesian coordinates, with three coordinates resulting from each residue, corresponding to the N, $C^\alpha$, and C' backbone atoms. Multiple mathematically equivalent formulations exist for this transformation; one suitable formulation is based on the Natural Extension Reference and described by the following set of equations:

$$\tilde{c}_k = r_{k \bmod 3} \begin{bmatrix} \cos(\theta_{k \bmod 3}) \\ \cos(\varphi_{[k/3], k \bmod 3})\sin(\theta_{k \bmod 3}) \\ \sin(\varphi_{[k/3], k \bmod 3})\sin(\theta_{k \bmod 3}) \end{bmatrix}$$

$$m_k = c_{k-1} - c_{k-2}$$

$$n_k = m_{k-1} \times \hat{m}_k$$

$$M_k = [\hat{m}_k, \hat{n}_k \times \hat{m}_k, \hat{n}_k]$$

$$c_k = M_k \tilde{c}_k + c_{k-1}$$

where $r_k$ is the length of the bond connecting atoms k−1 and k, $\theta_k$ is the bond angle formed by atoms k−2, k−1, and k;

$$\varphi_{\left[\frac{k}{3}\right], k \bmod 3}$$

is the predicted torsional angle formed by atoms k−2 and k−1, $c_k$ is the position of the newly predicted atom k; $\hat{m}$ is the unit-normalized version of m, and × is the cross product. Note that k indexes atoms 1 through 3L, since there are three backbone atoms per residue. For each residue t, $c_{3t-2}$, $c_{3t-1}$, and $c_{3t}$ are computed using the three predicted torsional angles of residue t, specifically $$\varphi_{t,j} = \varphi_{\left[\frac{3t}{3}\right], (3t+j) \bmod 3}$$

for j={0,1,2}.

The bond lengths and angles are fixed, with three bond lengths $(r_0, r_1, r_2)$ corresponding to N—$C^\alpha$, $C^\alpha$-C', and C'—N, and three bond angles $(\theta_0, \theta_1, \theta_2)$ corresponding to N—$C^\alpha$—C'. $C^\alpha$—C'—N, and C'—N—$C^\alpha$. As there are only three unique values we have $r_k = r_{k \bmod 3}$ and $\theta_k = \theta_{k \bmod 3}$.

The resulting sequence $(c_1 \ldots c_{3L})$ fully describes the protein backbone chain structure and represents the final predicted output. For training purposes a loss is necessary to optimize model parameters. In some embodiments, dRMSD metric is used as it is differentiable and captures both local and global aspects of protein structure. This metric is defined by the following set of equations:

$$\tilde{d}_{j,k} = \|c_j - c_k\|_2$$

-continued $$d_{j,k} = \tilde{d}_{j,k}^{(exp)} - \tilde{d}_{j,k}^{(pred)}$$

$$dRMSD = \frac{\|D\|_2}{L(L-1)}$$

where $\{d_{j,k}\}$ are the elements of matrix D, and $\tilde{d}_{j,k}^{(exp)}$ and $\tilde{d}_{j,k}^{(pred)}$ are computed using the coordinates of the experimental and predicted structures, respectively. In effect, the dRMSD computes the $l_2$-norm of the distances over distances, by first computing the pairwise distances between all atoms in both the predicted and experimental structures individually, and then computing the distances between those distances. For most experimental structures, the coordinates of some atoms are missing. They are excluded from the dRMSD by not computing the differences between their distances and the predicted ones.

RGN hyperparameters were manually fit, through sequential exploration of hyperparameter space, using repeated evaluations on the ProteinNet11 validation set and three evaluations on ProteinNet11 test set. Once chosen, the same hyperparameters were used to train RGNs on ProteinNet7-12 training sets. The validation sets were used to determine early stopping criteria, followed by single evaluations on the ProteinNet7-12 test sets to generate the final reported numbers (excepting ProteinNet11). One implementation included two bidirectional LSTM layers, each having 800 units per direction, and in which outputs from the two directions are first concatenated before being fed to the second layer. Input dropout set at 0.5 was used for both layers, and the alphabet size was set to 60 for the angularization layer. Inputs were duplicated and concatenated; this had a separate effect from decreasing dropout probability. LSTMs were random initialized with a uniform distribution with support [−0.01,0.01], while the alphabet was similarly initialized with support [−π, π]. ADAM was used as the optimizer, with a learning rate of 0.001, $\beta_2$=0.95 and $\beta_1$=0.99, and a batch size of 32. Gradients were clipped using norm rescaling with a threshold of 5.0. The loss function used for optimization was length-normalized dRMSD (i.e. dRMSD divided by protein length), which is distinct from the standard dRMSD use herein for reporting accuracies. RGNs are very seed-sensitive. As a result, a milestone scheme was used to restart underperforming models early. If a dRMSD loss milestone is not achieved by a given iteration, training is restarted with a new initialization seed. The following table summarizes the milestones, which were determined based on preliminary runs.

In general, eight models were started and, after surviving all milestones, were run for 250,000 iterations, at which point the lower performing half were discarded, and similarly at 500,000 iterations, ending with two models that were usually run for ~2.5M iterations. Once validation error stabilized, the learning rate was reduced by a factor of 10 to 0.0001, and run for a few thousand additional iterations to gain a small but detectable increase in accuracy before ending model training.

Assessment of Model Error

Machine learning models must be trained against as large a proportion of available data as possible to fit model parameters and then evaluated against a distinct test set to assess accuracy. Reliable evaluation is frequently complicated by unanticipated information leakage from the training set into the test set, especially for protein sequences which share an underlying evolutionary relationship. Partly to address this problem, the Critical Assessment of Protein Structure Prediction (CASP) was organized to assess methods in a blinded fashion, by testing predictors using sequences of solved structures that have not been publicly released. To assess RGNs we therefore sought to recreate the conditions of past CASPs by assembling the ProteinNet datasets. For every CASP from 7 through 12, we created a corresponding ProteinNet test set of CASP structures, and a ProteinNet training set of all sequences and structures publicly available prior to the start of that CASP. Using multiple CASP datasets enables a deeper and more thorough assessment that spans a broad range of dataset sizes than relying on the most recent CASP alone. We also adopted the CASP division of test structures into free modeling (FM) targets that assess prediction of novel folds, and template-based (TBM and TBM-hard) targets that assess prediction of folds with known homologs in the Protein Data Bank (PDB). We set aside a subset of the training data as a validation set, to determine when to stop model training and to further insulate training and test data.

ProteinNet datasets were used for all analyses described herein. RGN hyperparameters were fit by repeated evaluations on the ProteinNet 11 validation set followed by three evaluations on the ProteinNet 11 test set. Once chosen, the same hyperparameters were used to train models on ProteinNet 7-12 training sets, with a single evaluation made at the end on each test set (excepting ProteinNet 11) to generate the following Table 1:

TABLE S3

Validation set milestones for training RGNs. RGN validation performance was monitored during training, and if the shown accuracy milestones were not achieved by the given iteration number, training was terminated and a new model started.

| | | | | | | |
|---|---|---|---|---|---|---|
| ProteinNet 7 | Iteration | 1,000 | 5,000 | | | |
| | dRMSD (Å) | 14 | 13.6 | | | |
| ProteinNet 8 | Iteration | 1,000 | 5,000 | 20,000 | 50,000 | |
| | dRMSD (Å) | 13.4 | 13.2 | 12.6 | 12 | |
| ProteinNet 9 | Iteration | 1,000 | 5,000 | 20,000 | 50,000 | 100,000 |
| | dRMSD (Å) | 13 | 12.7 | 12.2 | 11.2 | 10.3 |
| ProteinNet 10 | Iteration | 1,000 | 5,000 | 20,000 | 50,000 | 100,000 |
| | dRMSD (Å) | 12.8 | 12.3 | 11.5 | 10.7 | 9.4 |
| ProteinNet 11 | Iteration | 1,000 | 5,000 | 10,000 | 100,000 | 150,000 |
| | dRMSD (Å) | 13.7 | 13.5 | 13.2 | 12.1 | 11.4 |
| ProteinNet 12 | Iteration | 1,000 | 5,000 | 20,000 | 50,000 | 100,000 |
| | dRMSD (Å) | 13.5 | 12.6 | 12.2 | 11.4 | 10.6 |

TABLE 1

Comparative accuracy of RGNs using dRMSD. The average dRMSD (lower is better) achieved by RGNs and the top five
servers at each CASP is shown for the novel folds (left) and known folds (right) categories. Numbers are based on common
set of structures predicted by top 5 servers during each CASP. A different RGN was trained for each CASP, using the corresponding
ProteinNet training set containing all sequences and structures available prior to the start of that CASP.

|  | FM (novel folds) category (Å) | | | | | | TBM (known folds) category (Å) | | | | | |
| --- | --- | --- | --- | --- | --- | --- | --- | --- | --- | --- | --- | --- |
|  | CASP7 | CASP8 | CASP9 | CASP10 | CASP11 | CASP12 | CASP7 | CASP8 | CASP9 | CASP10 | CASP11 | CASP12 |
| RGN | 9.3 | 7.3 | 8.7 | 10.0 | 8.5 | 10.7 | 5.6 | 5.9 | 6.5 | 6.9 | 7.4 | 6.9 |
| 1$^{st}$ Server | 9.3 | 8.3 | 9.0 | 10.3 | 9.3 | 11.0 | 4.0 | 4.3 | 5.2 | 5.3 | 5.8 | 4.7 |
| 2$^{nd}$ Server | 9.9 | 8.6 | 9.1 | 10.6 | 9.6 | 11.2 | 4.0 | 4.6 | 5.2 | 5.4 | 6.0 | 4.8 |
| 3$^{rd}$ Server | 10.0 | 9.2 | 9.7 | 10.9 | 11.2 | 11.3 | 4.1 | 4.8 | 5.4 | 5.7 | 6.5 | 5.6 |
| 4$^{th}$ Server | 10.1 | 9.9 | 10.1 | 11.7 | 11.7 | 11.4 | 4.2 | 5.0 | 5.4 | 5.9 | 6.8 | 5.8 |
| 5$^{th}$ Server | 10.4 | 10.4 | 13.5 | 12.0 | 12.9 | 13.0 | 4.8 | 5.0 | 5.5 | 7.2 | 6.9 | 5.9 |

Subsequently additional test set evaluations were made to generate the following Table S1, with one evaluation per number reported:

TABLE S1

Effect of dataset size on RGN accuracy. RGNs trained on ProteinNet (PN) training set X were tested on all CASP test sets subsequent to X (e.g.
RGN trained on ProteinNet 7 was tested on CASP 8-12) to assess the effect of data set size on model accuracy. Numbers shown are differences in
average dRMSD (lower is better) relative to RGNs trained and tested on matching data sets (i.e. trained on ProteinNet X and tested on CASP X.)

|  |  | FM (novel folds) test set (Å) | | | | | | TBM (known folds) test set (Å) | | | | | |
| --- | --- | --- | --- | --- | --- | --- | --- | --- | --- | --- | --- | --- |
|  |  | CASP12 | CASP11 | CASP10 | CA5P9 | CASP8 | CASP7 | CASP 12 | CASP11 | CASP10 | CASP9 | CASP8 | CASP7 |
| Training set | PN7 | +0.9 | +0.3 | +1.1 | +1.0 | +1.8 | 0 | +1.7 | +1.8 | +0.9 | +1.5 | +0.4 | 0 |
|  | PN8 | +0.6 | +0.2 | +1.2 | +0.3 | 0 |  | +1.4 | +1.0 | +0.2 | +0.9 | 0 |  |
|  | PN9 | 0 | +0.7 | +0.8 | 0 |  |  | +0.6 | +0.6 | 0 | 0 |  |  |
|  | PN10 | +0.5 | +1.2 | 0 |  |  |  | +0.6 | 0 | 0 |  |  |  |
|  | PN11 | +0.2 | 0 |  |  |  |  | +0.1 | 0 |  |  |  |  |
|  | PN12 | 0 |  |  |  |  |  | 0 |  |  |  |  |  |

Predicting New Folds without Co-Evolution

We first assessed RGNs on a difficult task: predicting novel protein folds without co-evolutionary data. FM structures served as targets for this exercise. Table 1 above compares the average dRMSD of RGN predictions on FM structures to the top five automated predictors in CASP 7-12, known as "servers" in CASP parlance.

On all CASPs, RGNs were found to have the best performance, even compared to servers that use co-evolution data. RGNs outperformed other methods at both short and long, multi-domain proteins, suggesting their performance is not limited to one regime (e.g. short single domain proteins), despite having no explicit knowledge of domain boundaries. While the margin between RGNs and the next-best server is small for most CASPs, such small gaps are representative of the differences between the top five performers in Table 1. In general, small gains in accuracy at the top end are difficult, with only minimal gains obtained over a ten-year time span from CASP 6 to CASP 11. More substantial gains were seen in CASP 12 due to the use of co-evolutionary information, but RGNs match these advances without using co-evolutionary data and by operating in a fundamentally distinct and complementary way. The accuracy gap between RGNs and other servers is highest on CASP 11, which benefits from having the RGN hyperparameters fit on the ProteinNet11 validation set, suggesting similar gains may be had by optimizing RGN hyperparameters for each dataset. (This would not correspond to overfitting, as only the validation set is used to fit hyperparameters, but would require substantially more compute resources for training.) ProteinNet datasets of earlier CASPs are smaller, which may have also reduced accuracy. To assess the contribution of dataset size to model error, we used RGNs trained on earlier ProteinNet datasets to predict later CASP test sets (Table S1). As expected, accuracy drops as datasets shrink.

The dRMSD metric does not require structures to be pre-aligned, and is consequently able to detect regions of high local concordance even when global concordance is poor. Because dRMSD assesses predictions at all length scales however, it penalizes large global deviations in proportion to their distance, which can result in very high error for far-apart regions. To obtain a complementary assessment of model accuracy, we also tested RGNs using TM scores, which are defined by the following equation:

$$TM\ score = \max\left[\frac{1}{L_{target}} \sum_{i}^{L_{aligned}} \frac{1}{1 + \left(\frac{d_i}{d_0(L_{target})}\right)^2}\right]$$

where $L_{target}$ and $L_{aligned}$ are the lengths of the full protein and the aligned region, respectively, $d_i$ is the distance between the $i^{th}$ residues in the experimental and predicted structures, and $$d_0(L_{target}) = 1.24\sqrt[3]{L_{target} - 15} - 1.8$$

is used to normalize scores. TM scores do require structures to be pre-aligned, and thus can penalize predictions with high local concordance if a global alignment cannot be found, but they are less sensitive to large deviations because they only compute error over the aligned regions. TM scores range from 0 to 1, with a score of <0.17 corresponding to a random unrelated protein, and >0.5 generally corresponding to the same protein fold (Xu and Zhang, 2010). Since TM scores are not invariant to reflections, they are computed for both the original and reflected RGN structures and use the higher of the two. Table S2 below compares TM scores of RGN predictions to CASP servers.

TABLE S2

Comparative accuracy of RGNs using TM score. The average TM score (higher is better, range is between 0 and 1) achieved by RGNs and the top five servers at each CASP is shown for the novel folds (left) and known folds (right) categories. Numbers are based on common set of structures predicted by top 5 servers during each CASP. A different RGN was trained for each CASP, using the corresponding ProteinNet training set containing all sequences and structures available prior to the start of that CASP.

|  | FM (novel folds) category (TM score) | | | | | | TBM (known folds) catagory (TM score) | | | | | |
| --- | --- | --- | --- | --- | --- | --- | --- | --- | --- | --- | --- | --- |
|  | CASP7 | CASP8 | CASP9 | CASP10 | CASP11 | CASP12 | CASP7 | CASP8 | CASP9 | CASP10 | CASP11 | CASP12 |
| RGN | 0.27 | 0.36 | 0.28 | 0.25 | 0.28 | 0.29 | 0.49 | 0.50 | 0.48 | 0.48 | 0.47 | 0.43 |
| 1$^{st}$ Server | 0.33 | 0.37 | 0.32 | 0.30 | 0.29 | 0.35 | 0.72 | 0.72 | 0.71 | 0.69 | 0.66 | 0.70 |
| 2$^{nd}$ Server | 0.30 | 0.33 | 0.32 | 0.29 | 0.27 | 0.33 | 0.71 | 0.70 | 0.71 | 0.68 | 0.66 | 0.70 |
| 3$^{rd}$ Server | 0.29 | 0.31 | 0.30 | 0.27 | 0.26 | 0.31 | 0.71 | 0.70 | 0.70 | 0.68 | 0.65 | 0.70 |
| 4$^{th}$ Server | 0.27 | 0.25 | 0.29 | 0.27 | 0.25 | 0.31 | 0.70 | 0.69 | 0.70 | 0.68 | 0.64 | 0.68 |
| 5$^{th}$ Server | 0.24 | 0.24 | 0.28 | 0.26 | 0.22 | 0.30 | 0.68 | 0.69 | 0.70 | 0.67 | 0.64 | 0.68 |

In general, RGNs rank among the top five servers, but do not consistently outperform all other methods as they do on dRMSD, possibly reflecting the lack of partial credit assignment by TM scores.

Predicting Known Folds without Templates

RGNs were also assessed on predicting known protein folds without experimental templates, a challenging task that provides an advantage to template-based methods. TBM structures served as targets for this purpose. Table 1 and S2 compare RGN predictions to top CASP servers using dRMSD and TM score, respectively. In general, RGNs underperform the very top CASP servers, all of which use templates, although ~60% of predictions are within 1.5 Å of the best-performing server.

Since RGNs do not use templates, this suggests that they learn generalizable aspects of protein structure, and their improved accuracy on TBM targets relative to FM reflects denser sampling in TBM regions of protein space. It is found that RGN performance robustly transfers to sequences with >40% sequence identity, predicting structures with a median dRMSD of ~5 Å, and then begins to deteriorate. There was little difference in dRMSD between 50% and 90% sequence identity, with substantial error remaining at 90%, which is suggestive of underfitting.

Template-based methods are particularly accurate where template and query sequences overlap, and are inaccurate where they do not; unfortunately, non-overlapping regions are often the regions of high biological interest. Errors in these critical non-overlapping regions can be masked by large overlapping regions, inflating overall accuracy. We have found CASP predictions to be correlated (average $R^2$=0.44) with template quality across length scales as previously reported, while RGN predictions were not (average $R^2$=0.06). Thus RGNs perform equally well on regions of proteins with experimental templates and on those without.

RGNs as described herein may be implemented by computer-executable instructions, such as program modules, that are executed by a conventional computer. Generally, program modules include routines, programs, objects, components, data structures, etc. that performs particular tasks or implement particular abstract data types. Those skilled in the art will appreciate that the invention may be practiced with various computer system configurations, including multi-processor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote computer-storage media including memory storage devices.

Any suitable programming language may be used to implement without undue experimentation the analytical functions described above. Illustratively, the programming language used may include TEN SORFLOW, C, C++, C*, FORTRAN, Java, Modula-2, Pascal, Prolog, Python, REXX, and/or JavaScript, for example. Further, it is not necessary that a single type of instruction or programming language be utilized in conjunction with the operation of the system and method of the invention. Rather, any number of different programming languages may be utilized as is necessary or desirable.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A system comprising:
a display;
a memory containing non-transitory machine-readable medium comprising machine executable code having stored thereon instructions;
a control system coupled to the memory comprising one or more processors, the control system configured to execute the machine executable code to cause the one or more processors to:
receive molecular data comprising a set of amino acid residues of a protein;
process the set of amino acid residues using a recurrent geometric network;
output a three dimensional map of the protein comprising three dimensional Cartesian coordinates; and
display the three dimensional map on the display; and
wherein the control system is further configured to compute deviations between predicted and experimental structures using a distance-based root mean square deviation metric.

2. The system of claim 1, wherein processing the set of amino acid residues using a recurrent geometric network further comprises:
determining an internal state for each residue of the set of amino acid residues;
integrating the internal state with the states of adjacent amino acid residues for each residue of the set of amino acid residues;
determining, based on the integrated internal states, geometric units from predicted torsional angles; and
translating geometric units to Cartesian coordinates.

3. The system of claim 1, wherein the control system is further configured to store, in a memory, the three dimensional map of the protein comprising three dimensional Cartesian coordinates.

4. The system of claim 1, wherein the control system uses a recurrent geometric network.

5. The system of claim 1, wherein control system network is optimized to minimize the distance-based root mean square deviation metric.

6. The system of claim 1, wherein the control system generates a fully differentiable map extending from sequence to structure.

7. A method of using a control system comprising:
receiving molecular data comprising a set of amino acid residues of a protein;
processing the set of amino acid residues using a recurrent geometric network;

outputting a three dimensional map of the protein comprising three dimensional Cartesian coordinates; and displaying the three dimensional map on the display; and wherein the control system is further configured to compute deviations between predicted and experimental structures using a distance-based root mean square deviation metric.

8. The method of claim 7, wherein processing the set of amino acid residues using a recurrent geometric network further comprises:

determining an internal state for each residue of the set of amino acid residues;

integrating the internal state with the states of adjacent amino acid residues for each residue of the set of amino acid residues;

determining, based on the integrated internal states, geometric units from predicted torsional angles; and translating geometric units to Cartesian coordinates.

9. The method of claim 7, wherein the control system is further configured to store, in a memory, the three dimensional map of the protein comprising three dimensional Cartesian coordinates.

10. The method of claim 7, wherein the control system uses a recurrent geometric network.

11. The method of claim 7, wherein the control system is optimized to minimize the distance-based root mean square deviation metric.

12. The method of claim 7, wherein the control system generates a fully differentiable map extending from sequence to structure.

* * * * *